(12) United States Patent
Fjeldheim et al.

(10) Patent No.: US 12,146,770 B2
(45) Date of Patent: Nov. 19, 2024

(54) SENSOR TESTING STATION

(71) Applicant: Autostore Technology AS, Nedre Vats (NO)

(72) Inventors: Ivar Fjeldheim, Haugesund (NO); Trond Austrheim, Etne (NO)

(73) Assignee: AutoStore Technology AS, Nedre Vats (NO)

( * ) Notice: Subject to any disclaimer, the term of this patent is extended or adjusted under 35 U.S.C. 154(b) by 190 days.

(21) Appl. No.: 17/796,020

(22) PCT Filed: Jan. 26, 2021

(86) PCT No.: PCT/EP2021/051779
§ 371 (c)(1),
(2) Date: Jul. 28, 2022

(87) PCT Pub. No.: WO2021/151906
PCT Pub. Date: Aug. 5, 2021

(65) Prior Publication Data
US 2023/0056161 A1    Feb. 23, 2023

(30) Foreign Application Priority Data
Jan. 31, 2020   (NO) ................................ 20200120

(51) Int. Cl.
| | |
|---|---|
| *A61L 2/24* | (2006.01) |
| *A61L 2/10* | (2006.01) |
| *B65G 1/04* | (2006.01) |
| *G01D 21/02* | (2006.01) |

(52) U.S. Cl.
CPC ............... *G01D 21/02* (2013.01); *A61L 2/10* (2013.01); *A61L 2/24* (2013.01); *B65G 1/0464* (2013.01);
(Continued)

(58) Field of Classification Search
CPC ....................................................... G01D 21/02
(Continued)

(56) References Cited

U.S. PATENT DOCUMENTS

| | | | |
|---|---|---|---|
| 2014/0115958 A1 | 5/2014 | Helene et al. | |
| 2019/0307077 A1 | 10/2019 | Lert, Jr. | |
| 2020/0277137 A1* | 9/2020 | Bastian, II | ............. B66F 9/065 |

FOREIGN PATENT DOCUMENTS

| | | |
|---|---|---|
| CN | 207844078 A | 9/2018 |
| CN | 109720830 A | 5/2019 |

(Continued)

OTHER PUBLICATIONS

International Search Report issued in PCT/EP2021/051779 on May 3, 2021 (6 pages).

(Continued)

*Primary Examiner* — Walter L Lindsay, Jr.
*Assistant Examiner* — Philip T Fadul
(74) *Attorney, Agent, or Firm* — Baker Botts L.L.P.

(57) ABSTRACT

A system performs measurements in storage containers for storing items. The storage containers are stored in an automated storage system including a framework structure forming a three-dimensional storage grid structure for storing the storage containers. The grid structure forms vertical storage columns each having a horizontal area defined by the size of an access opening of the vertical storage columns. A rail system is arranged on the framework structure defining the circumference of each access opening on top of each storage column. The rail system provides available routes for container handling vehicles handling and transferring the storage containers to and from the storage columns. The system further includes a testing station, accessible to a container handling vehicle via the rail system, with measuring equipment for measuring atmospheric conditions and for perform- (Continued)

ing measurements in said storage container. The testing station is configured to communicate measurement data to a computer system. The testing station includes an upper part to which a measuring platform with measuring equipment is attached, a lower part for holding a container, and connector for connecting the upper part and the lower part and the testing station includes a lifting device adapted to raise and lower the measuring platform.

13 Claims, 8 Drawing Sheets

(52) U.S. Cl.
CPC ........ *A61L 2202/11* (2013.01); *A61L 2202/14* (2013.01)

(58) Field of Classification Search
USPC ........................................................ 73/865.8
See application file for complete search history.

(56) References Cited

FOREIGN PATENT DOCUMENTS

| | | |
|---|---|---|
| CN | 110304388 A | 10/2019 |
| EP | 3326452 A1 | 5/2018 |
| NO | 317366 B1 | 10/2004 |
| WO | 2014/075937 A1 | 5/2014 |
| WO | 2014/090684 A1 | 6/2014 |
| WO | 2015/193278 A1 | 12/2015 |
| WO | 2016/166354 A1 | 10/2016 |
| WO | 2018/146304 A1 | 8/2018 |
| WO | 2019/115556 A1 | 6/2019 |
| WO | 2019/206971 A1 | 10/2019 |
| WO | 2019/229181 A1 | 12/2019 |

OTHER PUBLICATIONS

Written Opinion of the International Searching Authority issued in PCT/EP2021/051779 on May 3, 2021 (10 pages).
International Preliminary Report on Patentability from PCT/EP2021/051779 mailed on Jan. 7, 2022 (15 pages).
Norwegian Search Report issued in No. 20200120 mailed on Aug. 12, 2020 (2 pages).
Liu Jing, Office Action for Chinese Patent Application No. 2021800121894, pub. by CNIPA, dated Mar. 29, 2024, Beijing, 12 pages.
Hoffert, Rudi, Extended European Search Report for European patent application No. EP24160715.9, dated Jul. 11, 2024, 11 pages, published by the European Patent Office, Munich, Germany.

* cited by examiner

SENSOR TESTING STATION

FIELD OF THE INVENTION

The present invention relates to an automated storage and retrieval system for storage and retrieval of containers, in particular to a system and method for performing measurements in a container when placed in a testing station comprising measuring equipment.

BACKGROUND AND PRIOR ART

Figure 1:
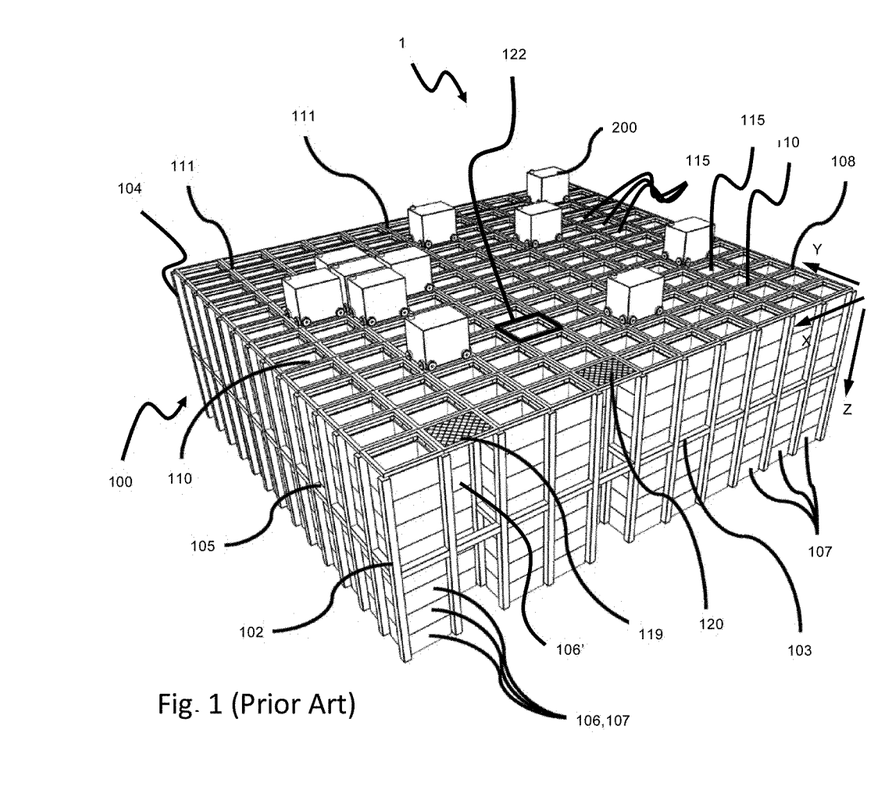
FIG. 1 is a perspective view of a framework structure of a prior art automated storage and retrieval system.
Figure 2:
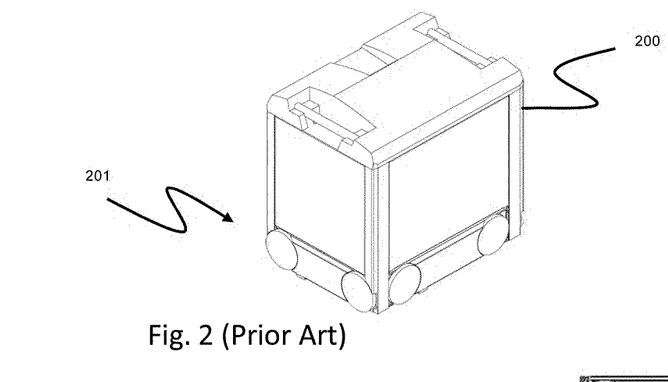
FIG. 2 is a perspective view of a prior art container handling vehicle having a centrally arranged cavity for carrying storage containers therein.
Figure 3:
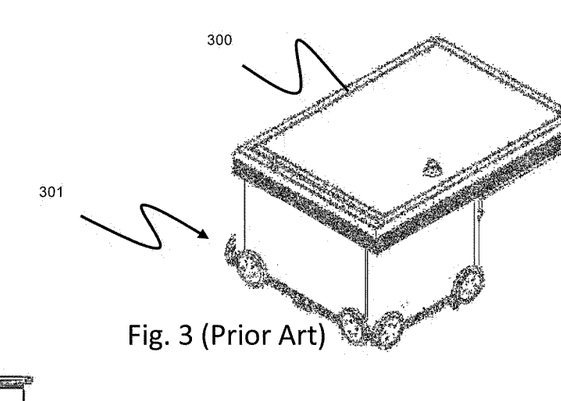
FIG. 3 is a perspective view of a prior art container handling vehicle having a cantilever for carrying storage containers underneath.

FIG. 1 discloses a typical prior art automated storage and retrieval system 1 with a framework structure 100 and FIGS. 2 and 3 discloses two different prior art container handling vehicles 201,301 suitable for operating on such a system 1.

The framework structure 100 comprises upright members 102, horizontal members 103 and a storage volume comprising storage columns 105 arranged in rows between the upright members 102 and the horizontal members 103. In these storage columns 105 storage containers 106, also known as bins, are stacked one on top of one another to form stacks 107. The members 102, 103 may typically be made of metal, e.g. extruded aluminum profiles.

The framework structure 100 of the automated storage and retrieval system 1 comprises a rail system 108 arranged across the top of framework structure 100, on which rail system 108 a plurality of container handling vehicles 201, 301 are operated to raise storage containers 106 from, and lower storage containers 106 into, the storage columns 105, and also to transport the storage containers 106 above the storage columns 105. The rail system 108 comprises a first set of parallel rails 110 arranged to guide movement of the container handling vehicles 201,301 in a first direction X across the top of the frame structure 100, and a second set of parallel rails 111 arranged perpendicular to the first set of rails 110 to guide movement of the container handling vehicles 201,301 in a second direction Y which is perpendicular to the first direction X. Containers 106 stored in the columns 105 are accessed by the container handling vehicles through access openings 112 in the rail system 108. The container handling vehicles 201,301 can move laterally above the storage columns 105, i.e. in a plane which is parallel to the horizontal X-Y plane.

The upright members 102 of the framework structure 100 may be used to guide the storage containers during raising of the containers out from and lowering of the containers into the columns 105. The stacks 107 of containers 106 are typically self-supportive.

Each prior art container handling vehicle 201,301 comprises a vehicle body 201a,301a, and first and second sets of wheels 201b,301b,201c,301c which enable the lateral movement of the container handling vehicles 201,301 in the X direction and in the Y direction, respectively. In FIGS. 2 and 3 two wheels in each set are fully visible. The first set of wheels 201b,301b is arranged to engage with two adjacent rails of the first set 110 of rails, and the second set of wheels 201c,301c is arranged to engage with two adjacent rails of the second set 111 of rails. At least one of set wheels 201b,301b,201c,301c can be lifted and lowered, so that the first set of wheels 201b,301b and/or the second set of wheels 201c,301c can be engaged with the respective set of rails 110, 111 at any one time.

Each prior art container handling vehicle 201,301 also comprises a lifting device (not shown) for vertical transportation of storage containers 106, e.g. raising a storage container 106 from, and lowering a storage container 106 into, a storage column 105. The lifting device comprises one or more gripping/engaging devices which are adapted to engage a storage container 106, and which gripping/engaging devices can be lowered from the vehicle 201,301 so that the position of the gripping/engaging devices with respect to the vehicle 201,301 can be adjusted in a third direction Z which is orthogonal the first direction X and the second direction Y. Parts of the gripping device of the container handling vehicle 301 is shown in FIG. 3 and is indicated with reference number 304. The gripping device of the container handling device 201 is located within the vehicle body 301a in FIG. 2.

Conventionally, and also for the purpose of this application, $Z=1$ identifies the uppermost layer of storage containers, i.e. the layer immediately below the rail system 108, $Z=2$ the second layer below the rail system 108, $Z=3$ the third layer etc. In the exemplary prior art disclosed in FIG. 1, $Z=8$ identifies the lowermost, bottom layer of storage containers. Similarly, $X=1 \ldots n$ and $Y=1 \ldots n$ identifies the position of each storage column 105 in the horizontal plane. Consequently, as an example, and using the Cartesian coordinate system X, Y, Z indicated in FIG. 1, the storage container identified as 106' in FIG. 1 can be said to occupy storage position $X=10$, $Y=2$, $Z=3$. The container handling vehicles 201,301 can be said to travel in layer $Z=0$, and each storage column 105 can be identified by its X and Y coordinates.

The storage volume of the framework structure 100 has often been referred to as a grid 104, where the possible storage positions within this grid is referred to as a storage cell. Each storage column may be identified by a position in an X- and Y-direction, while each storage cell may be identified by a container number in the X-, Y and Z-direction.

Each prior art container handling vehicle 201,301 comprises a storage compartment or space for receiving and stowing a storage container 106 when transporting the storage container 106 across the rail system 108. The storage space may comprise a cavity arranged centrally within the vehicle body 201a as shown in FIG. 2 and as described in e.g. WO2015/193278A1, the contents of which are incorporated herein by reference.

FIG. 3 shows an alternative configuration of a container handling vehicle 301 with a cantilever construction. Such a vehicle is described in detail in e.g. NO317366, the contents of which are also incorporated herein by reference.

The central cavity container handling vehicles 201 shown in FIG. 2 may have a footprint that covers an area with dimensions in the X and Y directions which is generally equal to the lateral extent of a storage column 105, e.g. as is described in WO2015/193278A1, the contents of which are incorporated herein by reference. The term 'lateral' used herein may mean 'horizontal'.

Alternatively, the central cavity container handling vehicles 101 may have a footprint which is larger than the lateral area defined by a storage column 105, e.g. as is disclosed in WO2014/090684A1.

The rail system 108 typically comprises rails with grooves into which the wheels of the vehicles are inserted. Alternatively, the rails may comprise upwardly protruding elements, where the wheels of the vehicles comprise flanges to prevent derailing. These grooves and upwardly protruding elements are collectively known as tracks. Each rail may comprise one track, or each rail may comprise two parallel tracks.

WO2018146304, the contents of which are incorporated herein by reference, illustrates a typical configuration of rail system 108 comprising rails and parallel tracks in both X and Y directions.

In the framework structure 100, a majority of the columns 105 are storage columns 105, i.e. columns 105 where storage containers 106 are stored in stacks 107. However, some columns 105 may have other purposes. In FIG. 1, columns 119 and 120 are such special-purpose columns used by the container handling vehicles 201,301 to drop off and/or pick up storage containers 106 so that they can be transported to an access station (not shown) where the storage containers 106 can be accessed from outside of the framework structure 100 or transferred out of or into the framework structure 100. Within the art, such a location is normally referred to as a 'port' and the column in which the port is located may be referred to as a 'port column' 119,120. The transportation to the access station may be in any direction, that is horizontal, tilted and/or vertical. For example, the storage containers 106 may be placed in a random or dedicated column 105 within the framework structure 100, then picked up by any container handling vehicle and transported to a port column 119,120 for further transportation to an access station. Note that the term 'tilted' means transportation of storage containers 106 having a general transportation orientation somewhere between horizontal and vertical.

In FIG. 1, the first port column 119 may for example be a dedicated drop-off port column where the container handling vehicles 201,301 can drop off storage containers 106 to be transported to an access or a transfer station, and the second port column 120 may be a dedicated pick-up port column where the container handling vehicles 201,301 can pick up storage containers 106 that have been transported from an access or a transfer station.

The access station may typically be a picking or a stocking station where product items are removed from or positioned into the storage containers 106. In a picking or a stocking station, the storage containers 106 are normally not removed from the automated storage and retrieval system 1, but are returned into the framework structure 100 again once accessed. A port can also be used for transferring storage containers to another storage facility (e.g. to another framework structure or to another automated storage and retrieval system), to a transport vehicle (e.g. a train or a lorry), or to a production facility.

A conveyor system comprising conveyors is normally employed to transport the storage containers between the port columns 119,120 and the access station.

If the port columns 119,120 and the access station are located at different levels, the conveyor system may comprise a lift device with a vertical component for transporting the storage containers 106 vertically between the port column 119,120 and the access station.

The conveyor system may be arranged to transfer storage containers 106 between different framework structures, e.g. as is described in WO2014/075937A1, the contents of which are incorporated herein by reference.

When a storage container 106 stored in one of the columns 105 disclosed in FIG. 1 is to be accessed, one of the container handling vehicles 201,301 is instructed to retrieve the target storage container 106 from its position and transport it to the drop-off port column 119. This operation involves moving the container handling vehicle 201,301 to a location above the storage column 105 in which the target storage container 106 is positioned, retrieving the storage container 106 from the storage column 105 using the container handling vehicle's 201,301 lifting device (not shown), and transporting the storage container 106 to the drop-off port column 119. If the target storage container 106 is located deep within a stack 107, i.e. with one or a plurality of other storage containers 106 positioned above the target storage container 106, the operation also involves temporarily moving the above-positioned storage containers prior to lifting the target storage container 106 from the storage column 105. This step, which is sometimes referred to as "digging" within the art, may be performed with the same container handling vehicle that is subsequently used for transporting the target storage container to the drop-off port column 119, or with one or a plurality of other cooperating container handling vehicles. Alternatively, or in addition, the automated storage and retrieval system 1 may have container handling vehicles specifically dedicated to the task of temporarily removing storage containers from a storage column 105. Once the target storage container 106 has been removed from the storage column 105, the temporarily removed storage containers can be repositioned into the original storage column 105. However, the removed storage containers may alternatively be relocated to other storage columns.

When a storage container 106 is to be stored in one of the columns 105, one of the container handling vehicles 201,301 is instructed to pick up the storage container 106 from the pick-up port column 120 and transport it to a location above the storage column 105 where it is to be stored. After any storage containers positioned at or above the target position within the storage column stack 107 have been removed, the container handling vehicle 201,301 positions the storage container 106 at the desired position. The removed storage containers may then be lowered back into the storage column 105, or relocated to other storage columns.

For monitoring and controlling the automated storage and retrieval system 1, e.g. monitoring and controlling the location of respective storage containers 106 within the framework structure 100, the content of each storage container 106; and the movement of the container handling vehicles 201,301 so that a desired storage container 106 can be delivered to the desired location at the desired time without the container handling vehicles 201,301 colliding with each other, the automated storage and retrieval system 1 comprises a control system 500 which typically is computerized and which typically comprises a database for keeping track of the storage containers 106.

Figure 4:
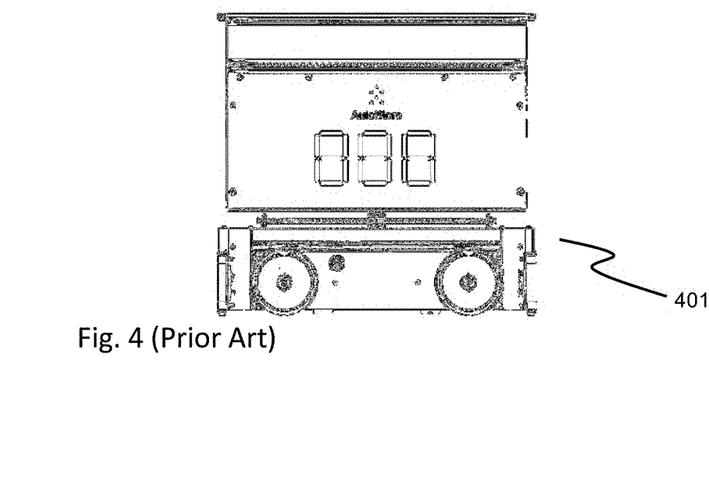
FIG. 4 is a side view of a delivery vehicle.
Figure 5A:
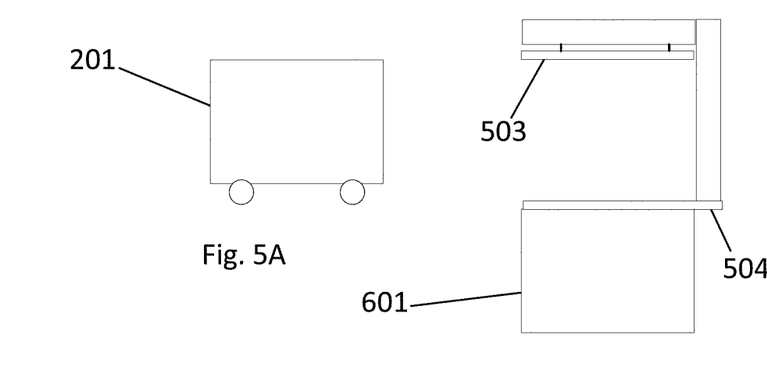
Figure 5B:
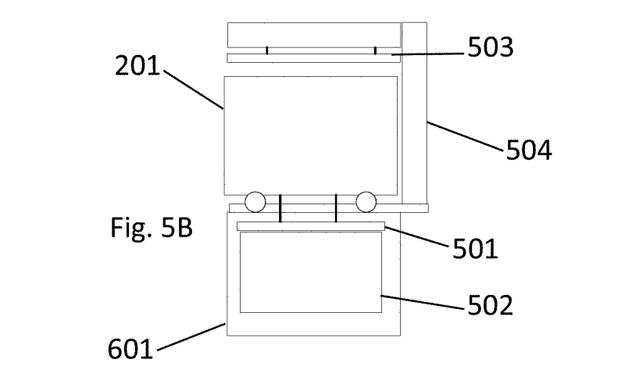
Figure 5C:
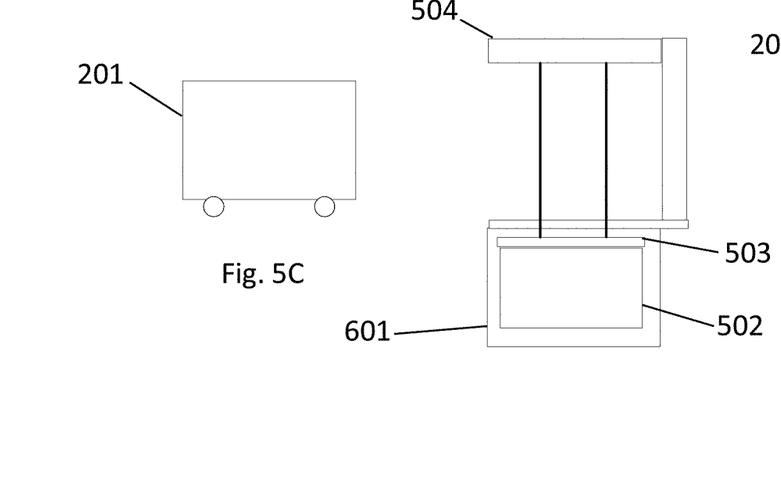
Figure 5D:
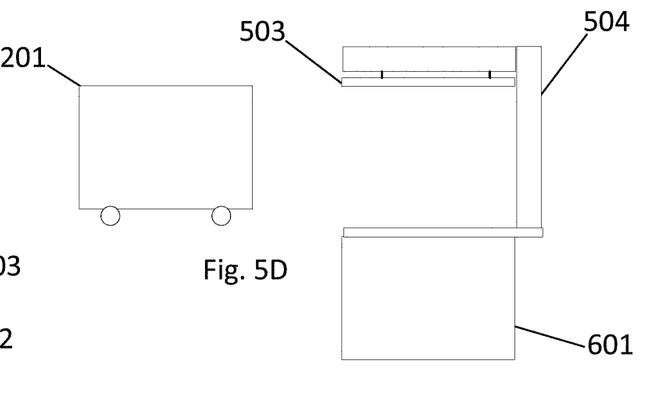
Figure 6A:
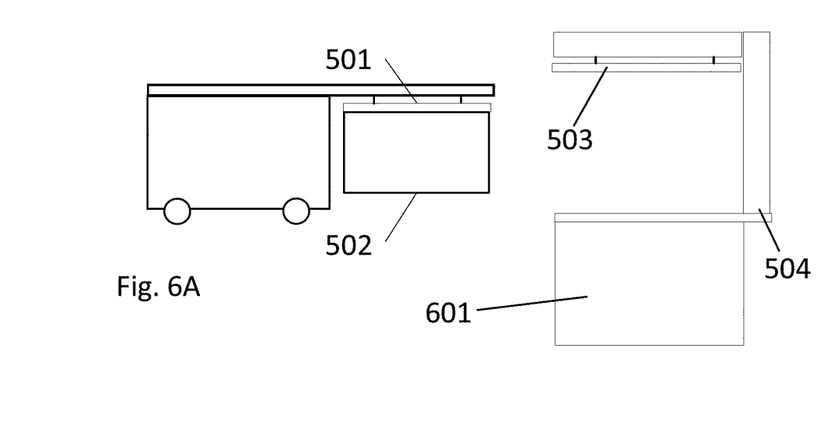
Figure 6B:
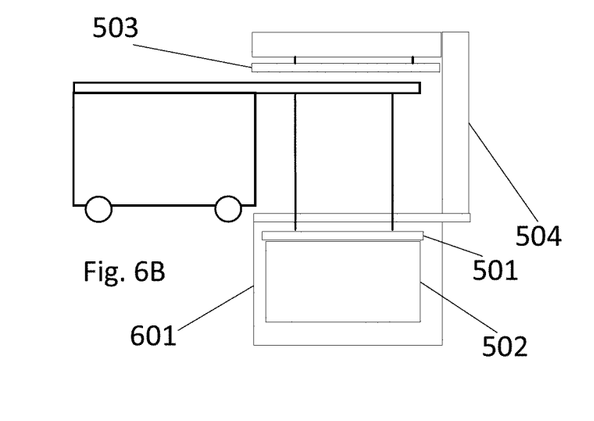
Figures 6C, 6D:
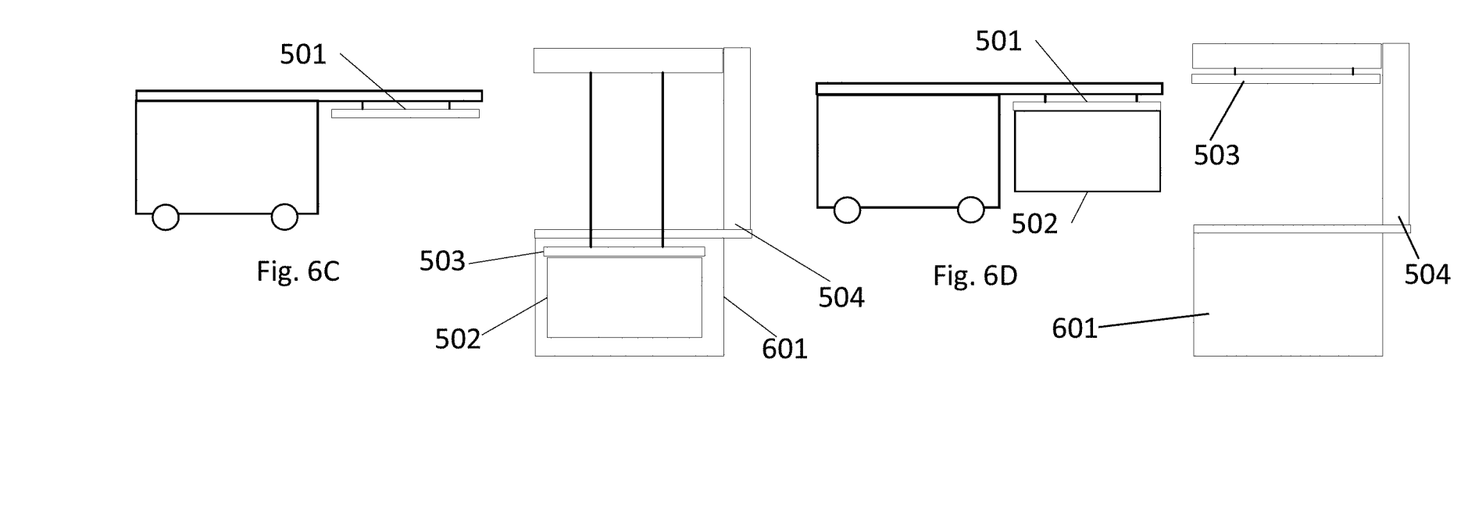
Figure 7A:
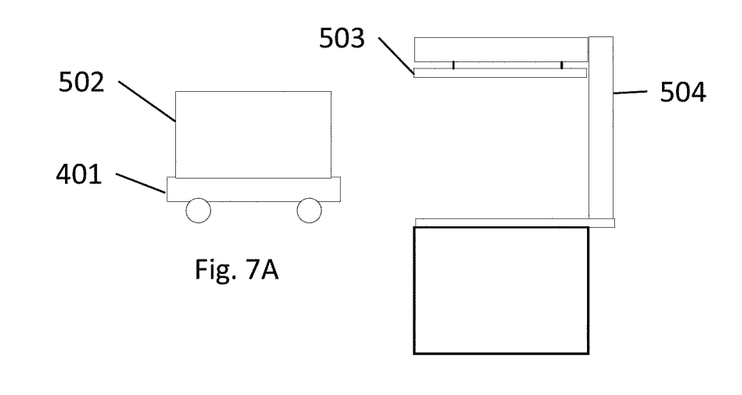
Figure 7B:
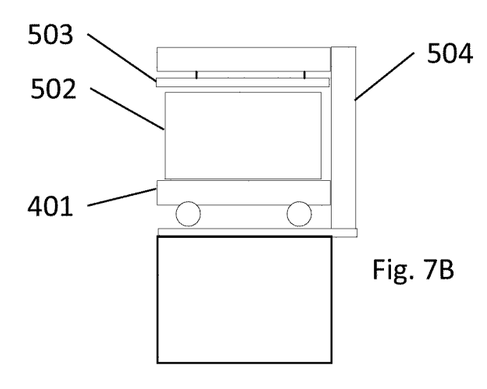
Figure 7C:
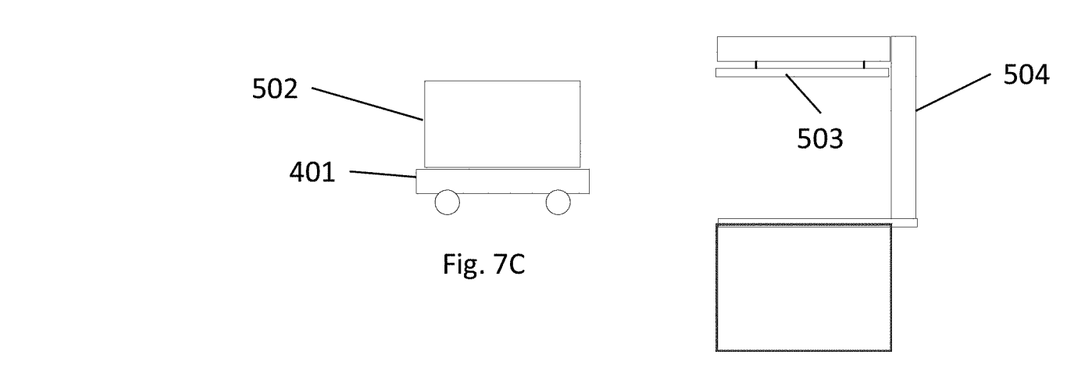
Figure 8A:
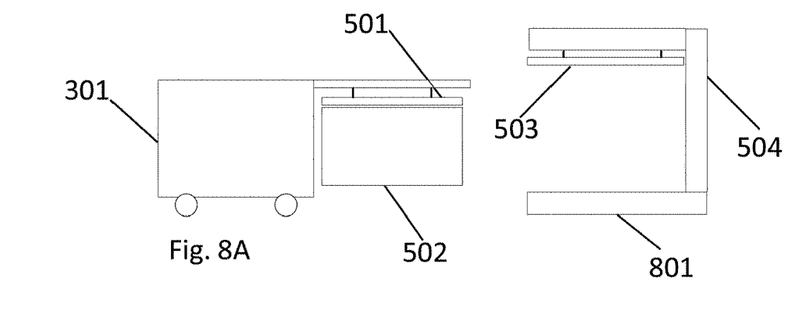
Figure 8B:
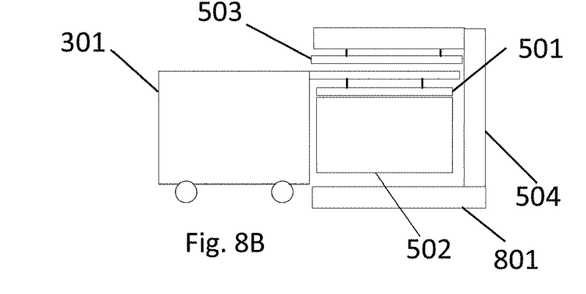
Figure 8C:
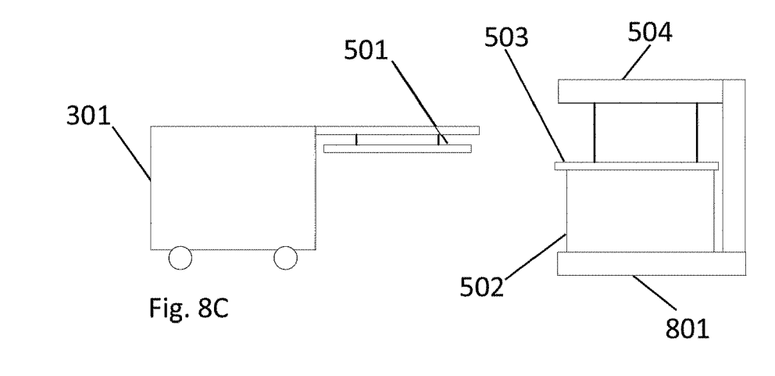
Figure 8D:
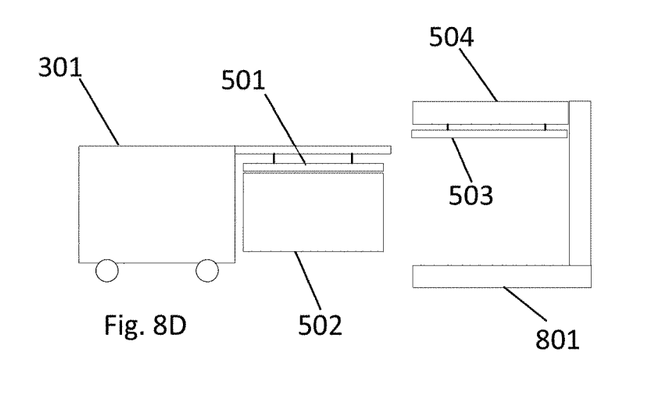

FIG. 4 describes a delivery vehicle. The delivery vehicles comprise a base with the same setup of wheels as on the container handling vehicles. The wheel base unit features a wheel arrangement having a first set of wheels for movement in a first direction upon a rail grid (i.e. any of the top rail grid and the transfer rail grid) and a second set of wheels for movement in a second direction perpendicular to the first direction. Each set of wheels comprises two pairs of wheels arranged on opposite sides of the wheel base unit. To change the direction in which the wheel base unit may travel upon the rail grid, one of the sets of wheels is connected to a wheel displacement assembly. The wheel displacement assembly is able to lift and lower the connected set of wheels relative to the other set of wheels such that only the set of wheels traveling in a desired direction is in contact with the rail grid. The wheel displacement assembly is driven by an electric motor. Further, two electric motors, powered by a rechargeable battery, are connected to the set of wheels to move the wheel base unit in the desired direction. The horizontal periphery of the wheel base unit is dimensioned to fit within the horizontal area defined by a grid cell of the rail grid such that two-wheel base units may pass each other on any adjacent grid cells of the rail grid. In other words, the wheel base unit may have a footprint, i.e. an extent in the X and Y directions, which is generally equal to the horizontal area of a grid cell, i.e. the extent of a grid cell in the X and Y directions, e.g. as is described in WO2015/193278A1, the contents of which are incorporated herein by reference.

A problem with the prior art solutions is that if there are perishable items in the storage there is a need for measuring the freshness of the products and the conditions the items are stored in. There is however a problem with getting accurate readings of the items without having to turn to costly solutions that require expensive equipment or extensive rebuilds. It is therefore an object of the present invention to solve the problems mentioned above.

SUMMARY OF THE INVENTION

The present invention is set forth and characterized in the independent claims, while the dependent claims describe other characteristics of the invention.

In one aspect, the invention is related to a system for performing measurements in storage containers for storing items, the storage containers are stored in an automated storage system comprising a framework structure forming a three-dimensional storage grid structure for storing the storage containers, where the grid structure forms vertical storage columns each having a horizontal area defined by the size of an access opening of the vertical storage columns and where a rail system is arranged on the framework structure defining the circumference of each access opening on top of each storage column, the rail system providing available routes for container handling vehicles handling and transferring the storage containers to and from the storage columns, and wherein said system is wherein the system further comprises a testing station, accessible to a container handling vehicle via the rail system, with measuring equipment for measuring atmospheric conditions and for performing measurements in said storage container and where the testing station is configured to communicate measurement data to a computer system Further the testing station may comprise an upper part to which the measuring platform is attached, a lower part for receiving the container and a part connecting the upper and the lower part. Also the testing station may have a space for accommodating a container between the upper and the lower part, and the testing station may be adapted to raise and lower the measuring platform.

The testing station may be adapted to accommodate a container handling vehicle with a container on top.

the measuring platform may be raised and lowered by a rope, band or wire controlled by an electric motor, or the measuring platform may be raised and lowered by a robotic arm, and the measuring platform comprises temperature measurement equipment, moisture detectors, gas detectors and cameras.

In a third aspect the invention is directed to a method of performing measurements in a container for storing in an automated storage system comprising a three-dimensional grid (4) of an underlying storage system (1), at least one container handling vehicle for transporting containers, ports for picking items for further distribution, a central computer system for controlling the operation of the storage system, and wherein said method comprises the steps of:
placing a container in a testing station by means of a container handling vehicle,
lowering a measuring platform attached to the testing station onto the container,
performing measurements, transmitting the measurements to the central computer system, performing an analysis based upon the measurements, transmitting instructions based on the analysis to a container handling vehicle, raising the measuring platform, transporting the container to another destination by means of a container handling vehicle. Performing measurements of temperature, moisture and gas level in the container and by using cameras for visual inspection of the items.

BRIEF DESCRIPTION OF THE DRAWINGS

Following drawings are appended to facilitate the understanding of the invention. The drawings show embodiments of the invention, which will now be described by way of example only, where:

FIG. 5A-D is a side view of an embodiment of the present invention wherein a container handling vehicle with a central cavity places a container in a testing station for measurements.

FIG. 6A-D is a side view of an embodiment of the present invention wherein a container handling vehicle with a cantilever solution places a container in a testing station for measurements.

FIG. 7A-C is a side view of an embodiment of the present invention wherein a delivery vehicle carrying a container is placed in a testing station.

FIG. 8A-D is a side view of an alternative embodiment of the present invention wherein a container handling vehicle with a cantilever solution places a container in a testing station for measurements.

FIG. 9A-C is a side view of an alternative embodiment of the present invention wherein a delivery vehicle carrying a container is placed in a testing station.

DETAILED DESCRIPTION OF THE INVENTION

In the following, embodiments of the invention will be discussed in more detail with reference to the appended drawings. It should be understood, however, that the drawings are not intended to limit the invention to the subject-matter depicted in the drawings.

The framework structure 100 of the automated storage and retrieval system 1 is constructed in accordance with the prior art framework structure 100 described above in connection with FIGS. 1-3, i.e. a number of upright members 102 and a number of horizontal members 103, which are supported by the upright members 102, and further that the framework structure 100 comprises a first, upper rail system 108 in the X direction and Y direction.

The framework structure 100 further comprises storage compartments in the form of storage columns 105 provided between the members 102, 103, where storage containers 106 are stackable in stacks 107 within the storage columns 105.

The framework structure 100 can be of any size. In particular it is understood that the framework structure can be considerably wider and/or longer and/or deeper than disclosed in FIG. 1. For example, the framework structure 100 may have a horizontal extent of more than 700×700 columns and a storage depth of more than twelve containers.

Embodiments of the automated storage and retrieval system according to the invention will now be discussed in more detail with reference to FIGS. 5A-D, 6A-D, 7A-C, 8A-D, 9A-C and 10.

In a preferred embodiment of the present invention the testing station is comprised of a top portion. This top portion houses the measuring platform. The measuring platform comprises at least one sensor. The at least one sensor is used to measure a at least one atmospheric condition in a storage container. One such atmospheric condition might be the temperature in the container, further the sensor can be used to detect the presence of gasses that is released during rotting of food. One such gas can be methane. Other gasses that are released during decay of food is carbon dioxide and hydrogen sulphide. In the case of carbon dioxide and hydrogen sulphide they are heavier than air and will therefore collect at the bottom of the container. The sensors for sensing carbon dioxide and hydrogen sulphide can therefore be attached to a probe that is lowered into the container. Alternatively there can be holes in the sides or in the bottom of the containers into which it is possible to insert sensors. In yet another solution there can be a slit or a tunnel e.g. along the inside edges of the container wherein the probe can be lowered into the bottom of the container without the content of the container hindering the probe. Further there can be detectors to detect moisture. The presence of moisture is due to the fact that during rotting of food the cells of the food is broken down and the liquid in the cells leaks out. A further type of measuring equipment can be a camera. The camera can take pictures into the container, i.e., of the contents, in order to detect if there is any sign of rotting food. The camera can be an ordinary camera that takes colour images in order to detect if there is marks on the food, like e.g., brown spots on bananas, or discoloration on the surface due to milldue. Alternatively or in addition, there can be used a camera that has ultraviolet light in order to detect mold.

There is also the possibility to use UV light in order to kill bacteria on the food. There is further a possibility to use UV light to kill mold. Therefor the measuring platform can have a UV light source that can be used to both detect rotting food and to kill bacteria and mold on the food and in the container. The difference between using the UV light source to detect decay and to kill bacteria and mold is the wavelength of the light and the power of the light source.

FIG. 5A-D is a side view of an embodiment of the present invention wherein a container handling vehicle with a central cavity places a container in a testing station for measurements. The container handling vehicle with a container in its central cavity moves into the testing station. The container is lowered down into a cavity underneath the container handling vehicle. After the container handling vehicle has placed the container in the testing station, the container handling vehicle moves away. After it has moved away, the measuring equipment is lowered down on a measuring platform. The testing station lowers a measuring platform onto the container. The measuring platform is lowered using lines attached to an electric motor. These lines can be wire, belts, chains, rope or similar. The measuring platform fits over the top opening. The platform further comprises measuring equipment attached to the underside. The measuring equipment is placed so that it fits inside the container when the platform is placed on the container. The measuring equipment can be a temperature sensor, a moisture sensor, a gas sensor and/or cameras. Any other kind of measuring equipment that can be mounted onto the measuring platform can be used. After the measuring equipment has collected the data, it can be sent to a central computer system. The central computer system can store the data together with the ID of the container in order to keep track of the condition of the content of the container. Based on the conditions of the content of the container, the central computer system can send instruction to a container handling vehicle to transport the container to a destination dependent on the condition of the items in the container. If the items are in a condition that is acceptable for distribution to customers, the container with the items are transported either to a station where the desired items can be picked for further distribution, or the container with the items can be transported back into the storage system. If one or more of the items in the container is of poor quality the container can be transported to a destination where the spoiled items can be removed from the container. After the items have been removed the container is either transported back to the storage system or to a port for further distribution to a picking station where items are picked for further distribution to customers.

FIG. 6A-D is a side view of an embodiment of the present invention wherein a container handling vehicle with a cantilever solution places a container in a testing station for measurements. The container handling vehicle approaches the testing station carrying a container from the storage system. The container handling vehicle places the container in the testing station. The container handling vehicle backs away giving the testing station access to the contents of the container via its top opening.

The testing station lowers a measuring platform onto the container. The measuring platform is lowered using lines attached to an electric motor. These lines can be wire, belts, chains, rope or similar. The measuring platform fits over the top opening. The platform comprises measuring equipment attached to the underside. The measuring equipment is placed, for example, on the underside, so that it fits inside the container when the platform is placed on the container. The measuring equipment can be a temperature sensor, a moisture sensor, a gas sensor and/or cameras. Any other kind of measuring equipment that can be mounted onto the measuring platform can be used. The collected data can be sent to a central computer system. The central computer system can store and analyse the data. The data can be stored together with the ID of the container in order to keep track of the condition of the content of the container. Based on the conditions of the content of the container, the central computer system can send instruction to a container handling vehicle to transport the container to a destination dependent on the condition of the items in the container. If the items are in a condition that is acceptable for distribution to customers, the container with the items are transported either to a station where the desired items can be picked for further distribution, or the container with the items can be transported back into the storage system. If one or more of the items in the container is of poor quality the container can be transported to a destination where the spoiled items can be removed from the container. After the items have been removed the container is either transported back to the storage system or to a port for further distribution to a picking station where items are picked for further distribution to customers.

FIG. 7A-D is a side view of an embodiment of the present invention wherein a delivery vehicle carrying a container is placed in a testing station. Since the delivery vehicle does not have a lifting platform arranged above the container, like the previously described handling vehicles, it is not possible for the delivery vehicle to place the container in the testing station with out help. In an embodiment of the present invention the delivery vehicle with the container on top therefor fits into the testing station. In this embodiment the testing station therefor has tracks in the bottom in order to allow the delivery vehicle to manouever itself with the container on top into the testing station. The testing station lowers the measuring platform onto the container. The measuring platform is lowered using, wire, belts, chains, rope or similar attached to an electric motor. The measuring platform fits over the top opening. The platform further comprises measuring equipment attached to the underside. The measuring equipment is placed so that it fits inside the container when the platform is placed on the container. The measuring equipment can be a temperature sensor, a moisture sensor, a gas sensor and/or cameras. Any other kind of measuring equipment that can be mounted onto the measuring platform can be used. After the data from the measuring equipment has been collected the data can be sent over to the central computer system. When the data is collected the delivery vehicle with the container on top can be transported to the next destination.

FIG. 8A-D is a side view of an alternative embodiment of the present invention wherein a container handling vehicle with a cantilever solution places a container in a testing station for measurements. The container handling vehicle approaches the testing station carrying a container from the storage system. The container handling vehicle places the container on the base of the testing station. The container handling vehicle backs away giving the testing station access to the contents of the container via its top opening. The testing station lowers a measuring platform onto the container. The measuring platform is lowered using, wire, belts, chains, rope or similar attached to an electric motor. The measuring platform fits over the top opening. The platform further comprises measuring equipment attached to the underside. The measuring equipment are placed so that it fits inside the container when the platform is placed on the container. The measuring equipment can be a temperature sensor, a moisture sensor, a gas sensor and/or cameras. Any other kind of measuring equipment that can be mounted onto the measuring platform can be used. The collected data can be sent to a central computer system. The central computer system can store and analyse the data. The data can be stored together with the ID of the container in order to keep track of the condition of the content of the container. Based on the conditions of the content of the container, the central computer system can send instruction to a container handling vehicle to transport the container to a destination dependent on the condition of the items in the container. If the items are in a condition that is acceptable for distribution to customers, the container with the items are transported either to a station where the desired items can be picked for further distribution, or the container with the items can be transported back into the storage system. If one or more of the items in the container is of poor quality the container can be transported to a destination where the spoiled items can be removed from the container. After the items have been removed the container is either transported back to the storage system or to a port for further distribution to a picking station where items are picked for further distribution to customers.

Figure 9A:
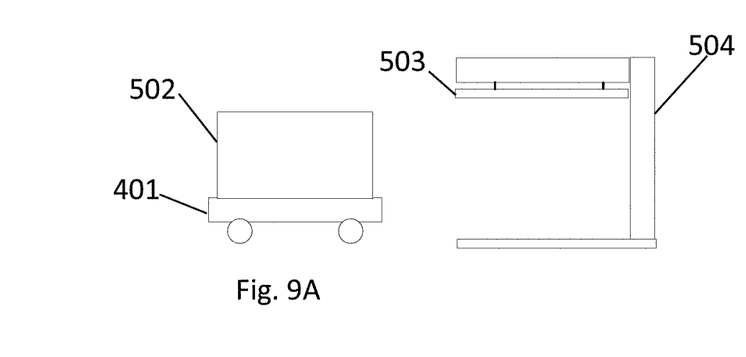
Figure 9B:
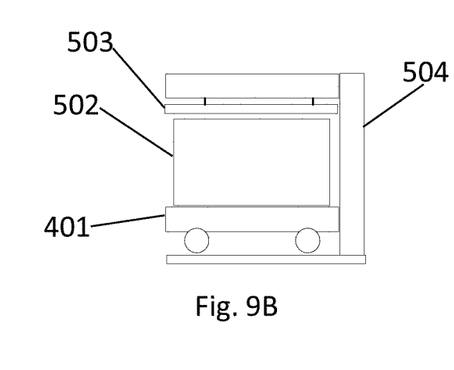
Figure 9C:
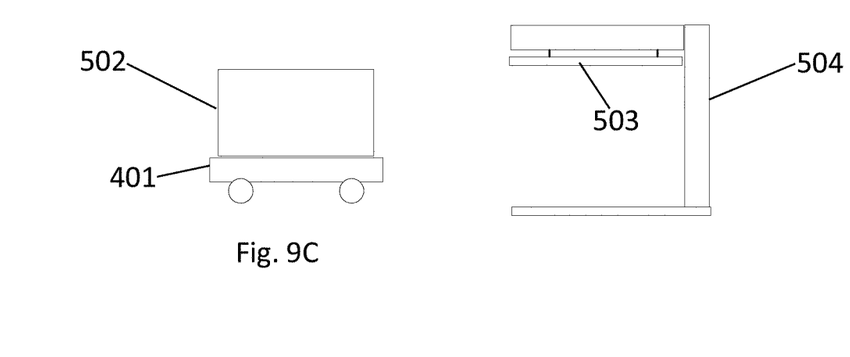

FIG. 9A-C is a side view of an alternative embodiment of the present invention wherein a delivery vehicle carrying a container is placed in a testing station. Since the delivery vehicle does not have a lifting platform holding the container it is not possible for the delivery vehicle to place the container in the testing station with out help. In an embodiment of the present invention the delivery vehicle with the container on top therefor fits into the testing station. In this embodiment the testing station has tracks in the base of the testing station in order to allow the delivery vehicle to manouever itself with the container on top into the testing station. The testing station lowers the measuring platform onto the container. The measuring platform is lowered using, wire, belts, chains, rope or similar attached to an electric motor. The measuring platform fits over the top opening. The platform further comprises measuring equipment attached to the underside. The measuring equipment are placed so that it fits inside the container when the platform is placed on the container. The measuring equipment can be a temperature sensor, a moisture sensor, a gas sensor and/or cameras. Any other kind of measuring equipment that can be mounted onto the measuring platform can be used. After the data from the measuring equipment has been collected the data can be sent over to the central computer system. When the data is collected the delivery vehicle with the container on top can be transported to the next destination.

Figure 10:
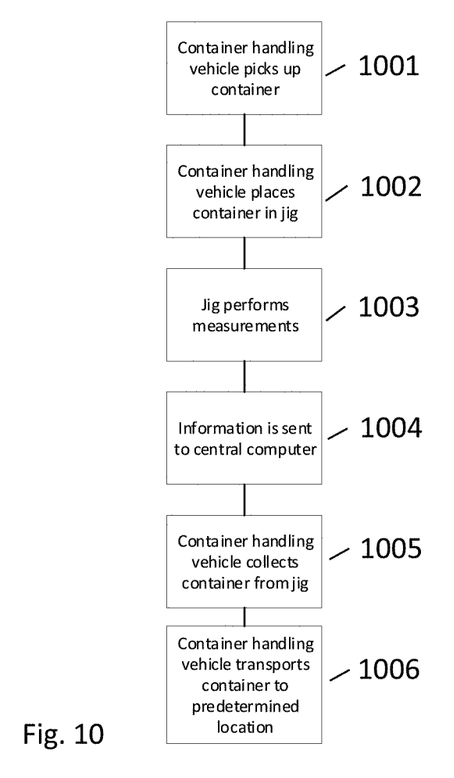
FIG. 10 is a flowchart describing the steps in the process of the embodiments of the present invention.

FIG. 10 is a flowchart describing the steps in the process of the embodiments of the present invention. A container handling vehicle or a delivery vehicle transports a container from the storage system. The storage system is an automated storage and retrieval system 1 with a framework structure 100, comprising upright members 102, horizontal members 103 and a storage volume comprising storage columns 105 arranged in rows between the upright members 102 and the horizontal members 103. In these storage columns 105 storage containers 106, also known as bins, are stacked one on top of one another to form stacks 107. The container handling vehicle or the delivery vehicle transports the container to the measuring station. Dependent on the vehicle transporting the container, the container is either placed in the testing station or the delivery vehicle with the container on top is parked in the testing station. The testing station lowers the measuring platform, the measuring platform fits over the top of the container. The measuring platform has sensors attached to it. The sensors can be a temperature sensor, a gas sensor, a moisture detector and/or a camera. The data from the sensors are collected and sent to the central computer system. In the central computer system the collected data is stored together with the ID of the container. Further the data can be analyzed and the result to the analysis is the basis for the conclusion of where the container and its content go after the measuring. After the measuring is performed, the central computer system sends instructions to the container handling vehicle or the delivery vehicle telling it to transport the container to a predetermined destination. The predetermined destination is dependent on the quality of the items in the container. If the items are of a quality that is good enough to be distributed to consumers, the container is either transported to a port and from there it is transported to a picking station where items are collected for further distribution, alternatively the container can be transported back to the storage grid structure. If the items in the container is of a quality that is not good enough for human consumption, it is transported to a destination where the spoiled items are picked from the container and disposed of according to prescribed instructions.

In the preceding description, various aspects of the delivery vehicle and the automated storage and retrieval system according to the invention have been described with reference to the illustrative embodiment. For purposes of explanation, specific numbers, systems and configurations were set forth in order to provide a thorough understanding of the system and its workings. However, this description is not intended to be construed in a limiting sense. Various modifications and variations of the illustrative embodiment, as well as other embodiments of the system, which are apparent to persons skilled in the art to which the disclosed subject matter pertains, are deemed to lie within the scope of the present invention.

LIST OF REFERENCE NUMBERS

Prior Art (FIGS. 1-10):
- 100 Framework structure
- 102 Upright members of framework structure
- 103 Horizontal members of framework structure
- 104 Storage grid
- 105 Storage column
- 106 Storage container
- 106' Particular position of storage container
- 107 Stack
- 108 Rail system
- 110 Parallel rails in first direction (X)
- 110a First rail in first direction (X)
- 110b Second rail in first direction (X)
- 111 Parallel rail in second direction (Y)
- 111a First rail of second direction (Y)
- 111b Second rail of second direction (Y)
- 112 Access opening
- 119 First port column
- 120 Second port column
- 201 Prior art storage container vehicle
- 201a Vehicle body of the storage container vehicle 101
- 201b Drive means/wheel arrangement, first direction (X)
- 201c Drive means/wheel arrangement, second direction (Y)
- 301 Prior art cantilever storage container vehicle
- 301a Vehicle body of the storage container vehicle 101
- 301b Drive means in first direction (X)
- 301c Drive means in second direction (Y)
- X First direction
- Y Second direction
- Z Third direction
- 401 Delivery vehicle
- 501 Container lifting platform
- 502 Container
- 503 Measuring platform
- 504 Testing station
- 601 Container placement area.
- 801 Plate

The invention claimed is:

1. A system for performing measurements in storage containers for storing items, the storage containers are stored in an automated storage system comprising a framework structure forming a three-dimensional storage grid structure for storing the storage containers, wherein the grid structure forms vertical storage columns each having a horizontal area defined by the size of an access opening of the vertical storage columns and wherein a rail system is arranged on the framework structure defining the circumference of each access opening on top of each storage column, the rail system providing available routes for container handling vehicles handling and transferring the storage containers to and from the storage columns, and wherein said system is further comprises a testing station, accessible to said container handling vehicle via the rail system, with measuring equipment for measuring atmospheric conditions and for performing measurements in said storage container and wherein the testing station is configured to communicate measurement data to a computer system, the testing station comprises an upper part to which a measuring platform with measuring equipment is attached, a lower part for holding said storage container, and connection means for connecting the upper part and the lower part and the testing station comprises a lifting device adapted to raise and lower the measuring platform.

2. The system according to claim 1, wherein the lower part comprises a cavity underneath a set of rails and into which said storage container can be lowered.

3. The system according to claim 1, wherein the lower part comprises a plate with a set of tracks on them.

4. The system according to claim 1, wherein the testing station comprises a space between the upper part and the lower part adapted for accommodating said storage container.

5. The system according to claim 1, wherein the testing station is adapted to accommodate said container handling vehicle with said storage container on top.

6. The system according to claim 1, wherein the measuring equipment is raised and lowered by a rope, band, or wire controlled by an electric motor.

7. The system according to claim 1, wherein the measuring equipment is raised and lowered by a robotic arm.

8. The system according to claim 1, wherein the measuring equipment comprises temperature measurement equipment, moisture detectors, gas detectors, and/or cameras.

9. The system according to claim 1, further comprising an UV light source for detecting mold on the items stored in the storage container.

10. The system according to claim 1, further comprising UV-C light source for killing mold, virus and bacteria on the items stored in the storage container.

11. A method for performing measurements in storage containers for storing items using a testing station, the storage containers are stored in an automated storage system comprising a framework structure forming a three-dimensional storage grid structure for storing the storage containers, wherein the grid structure forms vertical storage columns each having a horizontal area defined by the size of an access opening of the vertical storage columns and wherein a rail system is arranged on the framework structure defining the circumference of each access opening on top of each storage column, the rail system providing available routes for container handling vehicles handling and transferring the storage containers to and from the storage columns, each vehicle comprising a vehicle controller communicating with a central computer system controlling an operation of the storage system, and wherein said method comprises:
- placing said storage container in the testing station by means of said container handling vehicle,
- offering up a measuring equipment attached to the testing station onto the storage container,
- performing measurements to collect measurement data,
- transmitting the measurement data to a computer system,
- storing the transmitted measurement data and performing an analysis of the measurement data, transmitting instructions, regarding where to transport the container, from the central computer system to said container handling vehicle based on a result of the analysis,
raising the measuring equipment,
transporting the storage container to a next destination by means of said container handling vehicle.

12. The method according to claim 11, by performing measurements of temperature, moisture and/or gas level in the storage container and/or by using cameras for visual inspection of the items.

13. The method according to claim 12 wherein gas detectors are lowered into the storage container.

\* \* \* \* \*